United States Patent [19]
Gersten et al.

[11] Patent Number: 5,416,539
[45] Date of Patent: May 16, 1995

[54] COMPACT KERATOSCOPE WITH INTERCHANGEABLE CONES

[76] Inventors: Martin Gersten, 43 Strong Pl., Brooklyn, N.Y. 11231; Roy Maus, 542 48th St., Brooklyn, N.Y. 11220; Lars Tibbling, 555 Main St., New York, N.Y. 10044

[21] Appl. No.: 623,720
[22] PCT Filed: Oct. 25, 1990
[86] PCT No.: PCT/US90/06157
  § 371 Date: Jul. 24, 1992
  § 102(e) Date: Jul. 24, 1992
[87] PCT Pub. No.: WO91/13583
  PCT Pub. Date: Sep. 19, 1991

Related U.S. Application Data

[63] Continuation-in-part of Ser. No. 492,939, Mar. 13, 1990, Pat. No. 5,018,850, and Ser. No. 496,016, Mar. 20, 1990, Pat. No. 5,009,498.

[51] Int. Cl.$^6$ .............................................. A61B 3/10
[52] U.S. Cl. .................................... 351/212; 351/221
[58] Field of Search ............. 351/206, 208, 211, 212, 351/221

[56] References Cited

U.S. PATENT DOCUMENTS

| | | | |
|---|---|---|---|
| 3,639,043 | 2/1972 | Townsley | 351/212 |
| 3,797,921 | 3/1974 | Kilmer et al. | |
| 4,569,576 | 2/1986 | Karpov et al. | 351/212 |
| 4,685,140 | 8/1987 | Mount, II | 351/212 |
| 4,772,115 | 9/1988 | Gersten et al. | 351/212 |
| 4,779,973 | 10/1988 | Miller et al. | 351/212 |
| 4,863,260 | 9/1989 | Gersten et al. | 351/212 |
| 4,978,213 | 12/1990 | El Hage | 351/212 |
| 5,009,498 | 4/1991 | Gersten et al. | 351/212 |
| 5,018,850 | 5/1991 | Gersten et al. | 351/212 |

Primary Examiner—Ricky D. Shafer
Attorney, Agent, or Firm—Howard R. Popper

[57] ABSTRACT

A keratoscope image processing system having a compact keratoscope usable with a variety of light ring cones employs an improved cone and lightbox combination in which the light transmitting rings of the cone are more sharply defined by being positioned between incised opaque rings, and in which the lightbox has facets for mounting and heat-sinking a pair of laser diodes, a semi-toroidal cavity for mounting a ring-shaped fluorescent lamp for illuminating the cone and tunnels that direct the laser beams into the cone to intersect on the visual axis of the cone. The light box provides a surface for fixedly mounting a pair of mirrors that redirect the laser beams. The different cones are identified by patterns of light pervious spots illuminated from the lightbox and sensed by detectors mounted in the lightbox. Signals from the detectors modify the image processing in accordance with stored optical characteristics corresponding to the detected patterns.

16 Claims, 3 Drawing Sheets

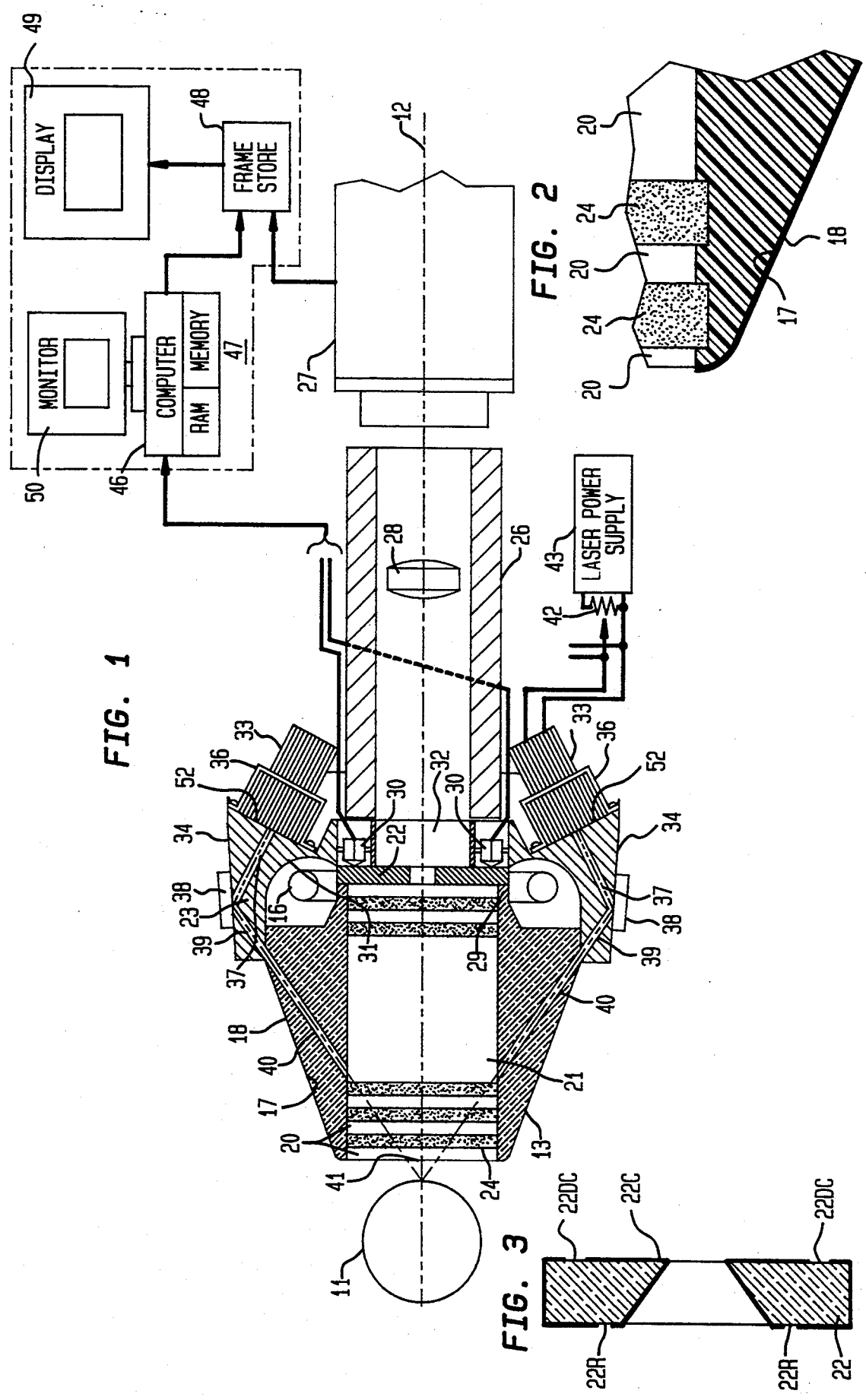

COMPACT KERATOSCOPE WITH INTERCHANGEABLE CONES

This application is a continuation-in-part of an application entitled "ILLUMINATED RING DEVICE", Ser. No. 07/492,939, Filed Mar. 13, 1990, now U.S. Pat. No. 5,018,850, and of an application entitled "INTERCHANGEABLE KERATOSCOPE DEVICE", Ser. No. 07/496,016, Filed Mar. 20, 1990, now U.S. Pat. No. 5,009,498, by the same inventors.

TECHNICAL FIELD

This invention relates to instruments for examining the topography of curved reflective surfaces, and more particularly, to such instruments known as keratoscopes.

BACKGROUND ART

Keratoscope instruments of the Placido disc type have long been used by ophthmologists for examining the surface curvature of the human eye. A more modern form of such instrument is disclosed in U.S. Pat. No. 3,797,921 issued Mar. 19, 1974 to L. G. Kilmer et al. The size of the Placido disc instrument is determined by the number of concentric light rings, or mires, to be projected onto the patient's eye and the more light rings that are to be projected in the vicinity of the limbus, the greater the diameter of the instrument must be. However the greater this dimension the more it tends to block eye contact between the patient and the ophthalmologist thereby causing certain patients some amount of emotional discomfort.

An improved form of apparatus for mapping the contours of the cornea is shown in Gersten, et al, U.S. Pat. No. 4,863,260 issued Sep. 5, 1989. The apparatus described in the Gersten '260 patent employed a cylindrical form of keratometer containing a plurality of illuminated rings incised along the opaquely coated bore of a conical translucent plastic body. The incised rings of the bore were illuminated by an array of incandescent lamps contained in a lightbox disposed adjacent to the base of the cone. Toward the apex of the cone converging beams from a pair of helium-neon laser guns established an optical reference point on the visual axis of the apparatus. For the precise location of the point of laser beam intersection it was desired to have the beams intersect at an appreciable angle of at least 90 degrees. Achieving this angle of intersection required that the laser guns either be positioned at this angle to the visual axis or that a mirror arrangement be employed. In either case the transverse dimension of the apparatus was increased.

As mentioned above, the illuminated rings of the Gersten et al '260 patent were formed by cutting through the opaque coating of the bore to expose the translucent plastic. Variations in the thickness of the opaque coating and in the sharpness of the tools used to cut through the opaque coating affected the regularity of the edges defining the illuminated rings and consequently the distinctness of the rings' image projected on the target. In addition, the plastic cone exhibited a substantial thermal coefficient of expansion. The array of incandescent lamps required to provide sufficient illumination to the base of the conical body to illuminate the incised rings could generate considerable heat. The expansion of the cone could shift the location of the ring pattern relative to the focal point of the instrument necessitating that the apparatus be recalibrated after warm-up. In addition, if it were desired to substitute a cone having a different ring pattern or different bore diameter a painstaking re-alignment of the laser beam guns and mirrors with respect to the visual axis of the apparatus would be required. Such substitution also would require re-programming of the computer controlling the mapping of the eye contour.

SUMMARY OF THE INVENTION

A more compact and versatile computer-controlled keratoscope system for producing sharper ring patterns and having the ability to employ an interchangeable variety of cones is provided through the use a structurally rigid lightbox which serves not only as a mounting for the different cones but which houses an improved light source and laser beam devices in such a manner as to eliminate any need for re-programming or subsequent adjustment by the user. The lightbox includes a polished, semi-toroidal concavity on its anterior face toward the base of the cone. A circular fluorescent lamp is positioned in the toroidal concavity so as to direct the lamplight toward the base of the cone. The opposite face of the lightbox provides facets for fixedly aligning a pair of laser diodes at a desired degree of inclination to the visual axis of the apparatus. Light beams from the laser diodes are conducted through a first pair of tunnels in the lightbox which lead to mirrors fixedly attached to an exterior surface of the lightbox. The mirrors redirect the laser beams into a second set of tunnels bored through the lightbox which are aligned with a third set of tunnels bored through the body of the plastic cone. The third set of tunnels lead the beam to intersect at the desired predetermined point on the visual axis of the apparatus.

In this illustrative embodiment, the predetermined alignment of the diodes, tunnels, mirrors, and the conical body made possible by the structurally rigid lightbox eliminates the need for alignment of the instrument by the user. Moreover, different conical bodies can be employed in the apparatus without require any adjustment in the alignment of the positions of the lasers, the point of intersection of their beams being unchanged.

Further in accordance with the principles of the present invention the interchangeability of the cones is facilitated by having each cone include a distinctive pattern of illuminated machine-readable indicator spots. The indicator spots are positioned so as to be illuminated from the lightbox and arranged in a code indicative of the calibration characteristics of the cone. The lightbox includes an array of photodetectors that are energized by the illuminated spots to indicate to the computer system a binary coded combination that identifies the particular type of cone that is in place.

In the illustrative embodiment, the light transmitting rings of the cone are not incised through the opaque coating. Instead, a series of rings are incised into a bare bore which is then opaquely coated, filling the incised rings. The bore is then reamed or slightly enlarged by machining to form uncoated, light-transmitting lands from which the coating has been removed between the incised rings. The walls and floor of the incised rings retain the opaque coating rather than the lands between the incised rings as in the prior art. Accordingly the thickness of the retained opaque coating is not as critical and the edges of the light transmitting rings are more sharply defined.

BRIEF DESCRIPTION OF DRAWINGS

A more complete understanding of the invention can be obtained from a consideration of the following detailed description and the appended claims in conjunction with the attached drawings in which:

FIG. 1 shows a keratoscope system including a top, cross-sectional view of an improved cone and lightbox;

FIG. 2 is an enlarged detail showing the rings of the cone of FIG. 1;

FIG. 3 is an enlarged cross-sectional view of the coded aperture disk of FIG. 1;

DETAILED DESCRIPTION

Figure 4A:
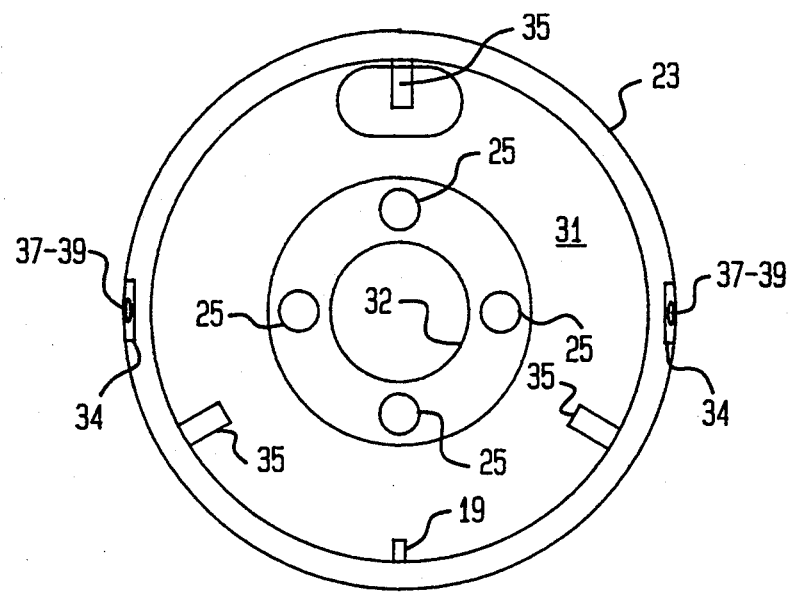
FIG. 4A is a front view of the anterior surface of the lightbox of FIG. 1.

FIG. 1 shows a computer-controlled keratoscope system having an improved cone 13 and lightbox 23. Target 11 is located at the apical end of cone 13 and is schematically indicated by a circle to represent the reflective surface of a calibration ball or the cornea of a patient's eye whose surface contour is to be mapped. A camera 27 acquires the two-dimensional image reflected from target 11. Computer-controlled subsystem 47 comprises a microcomputer 46, video monitor 49, frame store 48 and computer monitor 50 which displays a menu for guiding the operator through the processing steps.

The top cross-sectional view of cone 13 and lightbox 23 is taken along a horizontal plane through the visual axis 12. Cone 13 is fabricated of translucent plastic material and contains a central longitudinal cylindrical passageway 21 which is lined with a set of succesive illuminated rings 20 and opaque rings 24. The illuminated rings cause a corresponding set of illuminated mires to reflected from the reflective surface of target 11.

The exterior of cone 13 is provided with an inner, light reflective coating 17 and an outer opaque coating 18 to reflect as much of the light entering the base of the cone to the central passageway 21 so as to provide maximum illumination of rings 20.

The light-transmitting rings 20 of cone 13 are advantageously fabricated by first incising the series of annular rings 24 in central passageway 21, then coating the passageway with an opaque material, preferably black in color. The diameter of the passageway is then bored out to a depth less than that of the incised rings 24. This removes the opaque coating from the minor diameter of the passageway leaving a series of uncoated lands between the incised rings. The sidewalls and floors of the incised rings, however, retain the opaque coating.

In addition to the illuminated rings 20 provided along the bore 21, cone 13 may also advantageously be provided with an opaquely coated translucent disc 22 near its base end upon which one or more clear rings 22R (see FIG.3) may be provided. In addition, the base end of cone 13 may advantageoulsy contain a chamfered, uncoated extension portion 29 adjacent to the last of the translucent rings 20 which will light directly from lamp 16.

At the base of the cone 13 an aluminum lightbox 23 contains a semi-toroidal concavity 31 having a highly polished, reflective, interior surface. A circular fluorescent tube 16 is mounted in the concavity 31 and the reflective surface directs the light toward the base of cone 13.

An additional refinement is present in FIG. 1 in that fluorescent tube 16 and camera 27 may advantageously be chosen so that the phosphor employed in tube 16 is properly coordinated with the spectral response of the chip employed in camera 27. Matching the spectral responses provides better sensitivity of camera focus. However, it is important in a corneal measuring device that focus be achieved within the visible light spectrum. For example, where camera 27 employs a CCD chip, its spectral response may be found to be peaked toward the infra-red end of the light spectrum. Since it is undesirable to base corneal image measurements on infra-red response, the use of a fluorescent phosphor in tube 16 which produces no infra-red output is highly desirable. In addition, the color of the phosphor may advantageously be specified as green because the reflectivity of the human iris is lower for green so that the corneal image will have a "blacker" background between the illuminated rings due to the reduced amount of reflection than would occur with a white phosphor.

The image of the mires appearing on target 11 is reflected, back along the passage 21 through the central aperture of translucent disk 22 and the central aperture 32 of lightbox 23. The image is detected by camera subsystem including an extension tube 26, a camera 27, and a lens 28, all also coaxial with the visual axis 12. Camera 27 is advantageously focused at the focal point of the reflective surface of target 11, rather than the end 41 of cone 13 in order accurately to capture all of the rings reflected from the cornea.

To accommodate targets of different diameter and to project different kinds of ring patterns, different kinds of cones are required. The number of rings to be projected on the target is determined by the length and diameter of cone 13. In order to distinguish automatically among the different types of cones that may be mounted to lightbox 23, each cone is provided with a an opaquely coated aperatured plastic disk 22 having a distinctive plurality of binary-coded markings 22DC on its right-hand side. Such markings are provided by selectively removing a portion of the opaque coating 22C of disk 22 except at selected ones of those coded locations necessary to indicate which of plural conical body types is in place. When fluorescent tube 16 is energized, the interior of aperatured disk 22 is illuminated and photosensors 30 mounted in the lightbox 23 respond to the pattern of illumination provided by the binary coded markings 22DC on disk 22.

A pair of laser diodes 33 are mounted on respective facets or bosses 52 on the posterior face of lightbox 23 opposite concavity 31. Laser diodes 33 have their longitudinal axes in a common plane with the visual axis 12 and are located as close as possible to axis 12 so that the keratoscope can have small lateral dimensions. Facets 52 are oriented so that the beams from the lasers 33 are angled away from the axis 12. Light beams from lasers 33 are projected through a first set of tunnels 37 bored in lightbox 23. The beams emerge at the periphery of lightbox 23 where they are reflected by mirrors 38 into a second set of tunnels 39 aimed at intersection point 41 on visual axis 12. Mirrors 38 are adhesively bonded to the exterior surface lightbox 23.

Tunnels 39 are collinear with a third pair of tunnels 40, respectively, in cone 13. Tunnels 40 are in the same common plane with axis 12. Tunnels 37 and 39 are angled so that mirrors 38 will steer the laser beams from tunnels 37 through tunnels 39 and 40 to predetermined intersection point on visual axis 12. Since beams from lasers 33 are enclosed within a series of tunnels whose alignment is fixed, they are not subject to misalignment nor are they subject to external interference.

Laser diodes 33 generate some heat and their characteristics have some known temperature sensitivities. The thermal mass of aluminum lightbox 23 in conjunction with the use of thermally conductive mounting brackets 36 provide an effective heat sink to stabilize the temperature of the diodes. Each of the lasers 33 is connected to the tap terminals of a potentiometer 42 at the output of a laser power supply 43 to determine the operating power level of the lasers.

Suitable diode lasers are presently commercially available from several different manufacturers. One such diode laser operates at a wavelength of 670 nanometers, well within the visible spectrum, and an output power of about ten microwatts. Coherent beam waist diameter is about 270 microns. The laser is in a gold plated metallic housing that is about 2.5 centimeters long, including internal focusing optics.

It can be seen from the foregoing description that lightbox 23 provides a platform providing common support for a group of keratoscope parts including cone 13, circular fluorescent light tube 16, photosensors 30, lasers 33, and mirrors 38.

Figure 4B:
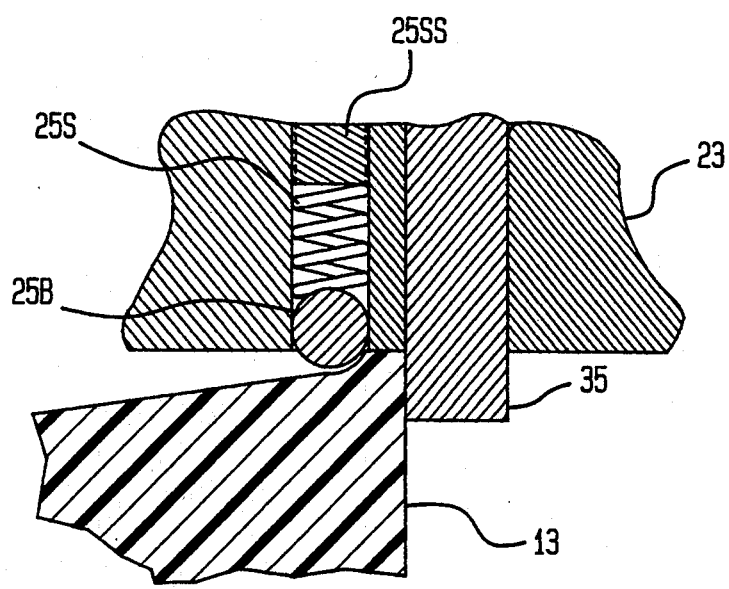
FIG. 4B is a detail of the mechanism for retaining the interchangeable light cones.

While FIG. 1 shows a top cross-sectional view of lightbox 23 in order to best illustrate tunnels 37 and 39, FIG. 4A shows a frontal view of lightbox 23. At the "6-o'clock" position of lightbox 23, a single locating key 19 engages a slot in the base of cone 13 to radially orient cone 13 in lightbox 23. At the "12-o'clock" "4-o'clock" and "8-o'clock" positions of lightbox 23 a banking pin 35 and a spring loaded detent ball (shown in FIG. 4B) removably secure cone 13 in lightbox 23. The relationship of the lightbox's detent ball 25B, spring 25S, and retaining set screw 25SS with the base of cone 13 is shown in FIG. 4B. At the "9-o'clock and "3-o'clock" positions in the rim of lightbox 23 are seen the ends 61 of tunnels 37 and 39 of FIG. 1 where these tunnels meet at mirror-mounting flats 34. At the "12-o'clock" position of lightbox 23 a pass-through hole 54 accommodates the ends (not shown) of the fluorescent tube 16 so that electrical connections (not shown) can be made without throwing shadows onto the base of cone 13. Tube 16 (FIG. 1) is advantageously fixed in place within the concavity 31 with several dabs of silicone glue. Central opening 32 provides for the passage of light along the visual axis 12 as shown in FIG. 1. Through internal rim 58 four holes 25 are provided for retaining the photosensors 30 (of FIG. 1).

Figure 5:
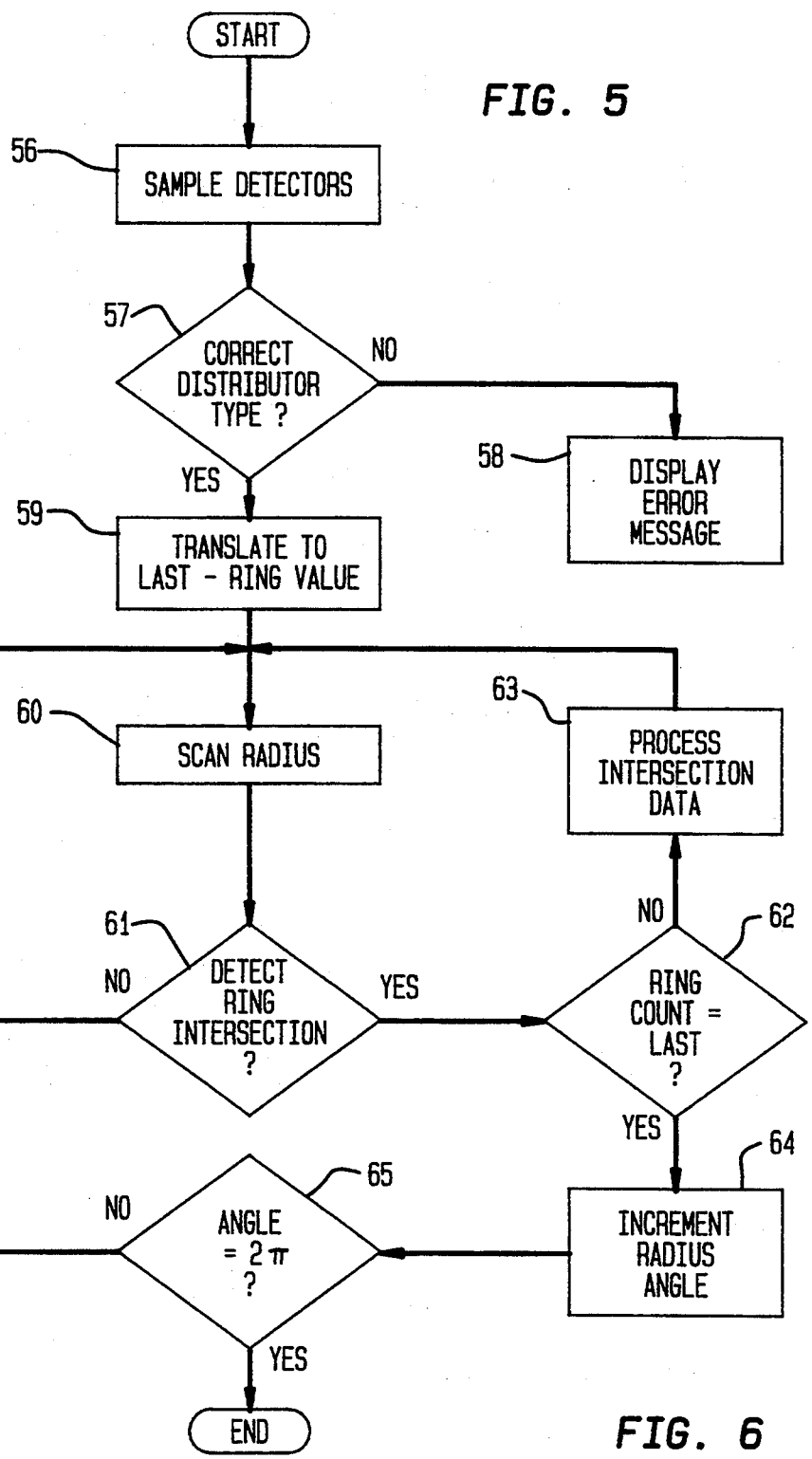
FIG. 5 is a process flow diagram for responding to the cone type indicator signals.
Figure 6:
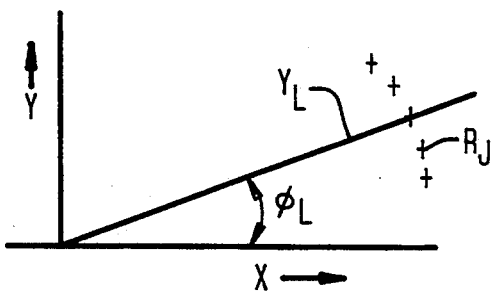
FIG. 6 is a diagram of image data scanning parameters used in FIG. 5.

FIG. 5 is a process flow diagram illustrating one way to incorporate the use of coded indicator spots 22DC into one well-known radial scanning routine for keratoscopic image data processing. Reference characters in parentheses correspond to similarly designated steps in FIG. 5. FIG. 6 is a diagram to facilitate consideration of FIG. 5 and shows an arbitrary radius ri extending from a center point at the X-Y axis origin, at an arbitrary angle $\phi i$ with respect to the X-axis. That center point represents a central point in an image. Image data points for a last-ring Ri are also shown.

At the start of the FIG. 5 process, outputs of photosensors 30 are sampled (56) and tested to ascertain correct cone type (57) by using user-provided initializing input data stored in the memory of microcomputer 46. If it is not one for which data has been stored, an error message is displayed (58); and the process is interrupted until corrective action is taken. If the proper ring device type is in place, the value represented by the binary coded, detector states information is translated (59) to obtain a last-ring count value for the particular application involved and which count will be used to limit the extent of scanning along different radii from a predetermined display center point to locate intersections with reflected images of illuminated rings 20.

An initial radius scan is begun (60). At successive points along the radius ri, image picture element intensity values are compared to detect (61) intersections with reflections of bright illuminated rings 20. If no intersection is detected the test location is incremented out along the radius to make a new test. If an intersection is detected, a count of intersections found so far in the scan is compared (62) to the last-ring count from step (59). If the last-ring Ri has not been reached, the intersection data is processed (63); and the scan location is incremented again. If the last ring has been reached, the radius angle $\phi i$ is incremented (64) and the new angle checked (65) to see whether or not a full circular scan has been completed. If it has, the process ends; but if it has not, a scan from center at the new radius angle is begun (60).

Although the invention has been described in connection with a particular embodiment thereof, other applications, embodiments, and modifications which will be apparent to those skilled in the art are included within the spirit and scope of the invention.

What is claimed is:

1. A keratoscope image processing system for processing an image reflected upon a target, said system comprising a lightbox and a conical body of translucent material, said conical body having an integral cylindrical bore including a base portion, said cylindrical bore defining a series of successive opaque and light transmitting rings for reflection upon said target, said opaque rings being incised in said cylindrical bore and filled with an opaque coating, and said lightbox including a semi-toroidal concavity for accommodating a toroidal light source and for maintaining said light source substantially at the focus of said concavity, thereby to cause substantially all of the light from said light source to be transmitted toward the base portion of said conical body.

2. A keratoscope image processing system according to claim 1 wherein said light source is a fluorescent lamp.

3. A keratoscope image processing system according to claim 1 wherein said lightbox for accommodating said light source is an aluminum housing and wherein said semi-toroidal concavity is provided with a specular reflective surface.

4. A keratoscope image processing system according to claim 3 wherein said lightbox includes a recess for receiving the base portion of said conical body and a plurality of spring-loaded detents for removably securing said conical body in said recess.

5. A keratoscope image processing system according to claim 1 wherein said lightbox for accommodating said light source is an aluminum housing having an articulated facet for mounting and heat-sinking a diode laser.

6. A keratoscope image processing system according to claim 5 wherein said lightbox includes a first tunnel leading from said articulated facet for passage of a laser beam from said laser through said conical body.

7. A keratoscope image processing system according to claim 6 wherein said lightbox includes a second tunnel adjoining said first tunnel and a mirror positioned at the junction of said first and second tunnels.

8. A keratoscope image processing system according to claim 7 wherein said conical body includes a third tunnel, the axis of said third tunnel being adapted to be aligned with the axis of said second tunnel of said lightbox.

9. A keratoscope image processing system according to claim 8 wherein the axes of said second tunnel of said lightbox and said third tunnel of said conical body aim at a predetermined point in said bore.

10. A keratoscope image processing system according to claim 6 wherein the axis of said first tunnel is perpendicular to said articulated facet.

11. A keratoscope image processing system according to claim 5 wherein said lightbox includes a concave surface and wherein said articulated facet is located posteriorly to said concave surface.

12. A keratoscope image processing system according to claim 5 further comprising means for adjusting the power output of said laser.

13. A keratoscope image processing system according to claim 1 wherein said conical body includes a disc of translucent material disposed in said bore to receive a portion of the light introduced into said concavity and a plurality of light-pervious machine readable spots arranged on said disc.

14. A keratoscope image processing system according to claim 1 wherein said lightbox includes a key for maintaining said conical body in alignment with said lightbox.

15. A keratoscope image processing system according to claim 1 wherein said conical body includes a disc of translucent material disposed in said bore to receive a portion of the light introduced into said concavity, and said lightbox includes a recess for receiving said base portion of said conical body, a plurality of light-sensing diodes disposed to monitor the light transmitted through said disc, and means for coupling an output of said light-sensing diodes to said processing means, said processing means being responsive to said output to compensate for said series of opaque and light transmitting rings identified by said pattern.

16. A keratoscope image processing system according to claim 15, said system including means for storing a signal value representing a predetermined type of illuminated ring device, and means responsive to said output of said diodes including means for comparing said output with said signal value for modifying said processing of said keratoscope image.

* * * * *